US009333296B2

(12) United States Patent
Arnold et al.

(10) Patent No.: US 9,333,296 B2
(45) Date of Patent: May 10, 2016

(54) DISPOSABLE INSERTER FOR USE WITH A MEDICAL DEVICE

(71) Applicant: Roche Diagnostics Operations, Inc., Indianapolis, IN (US)

(72) Inventors: Ofer Arnold, Ha'movil (IL); Illai J Gescheit, Tel Aviv (IL); Avraham Neta, Gilon (IL)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 14/562,881

(22) Filed: Dec. 8, 2014

(65) Prior Publication Data

US 2015/0094688 A1 Apr. 2, 2015

Related U.S. Application Data

(63) Continuation of application No. PCT/EP2013/001685, filed on Jun. 8, 2013.

(60) Provisional application No. 61/657,771, filed on Jun. 9, 2012.

(51) Int. Cl.
*A61M 31/00* (2006.01)
*A61M 5/158* (2006.01)
*A61M 5/50* (2006.01)

(52) U.S. Cl.
CPC .............. *A61M 5/158* (2013.01); *A61M 5/5086* (2013.01); *A61M 2005/1585* (2013.01); *A61M 2005/1586* (2013.01); *A61M 2005/1588* (2013.01)

(58) Field of Classification Search
CPC ........... A61M 2005/14252; A61M 2005/1426; A61M 2005/1581; A61M 2005/1585
USPC .......................... 604/506, 198, 192, 272, 180
See application file for complete search history.

(56) References Cited

U.S. PATENT DOCUMENTS

2008/0319414 A1* 12/2008 Yodfat ................. A61B 5/6849
604/506

* cited by examiner

*Primary Examiner* — Phillip Gray
(74) *Attorney, Agent, or Firm* — Dinsmore & Shohl LLP

(57) ABSTRACT

An inserter and methods of using embodiments of the inserter are described. The inserter includes a housing having a cannula assembly and an insertion mechanism. Two buttons are located on the inserter and are concomitantly actionable for actuation of the insertion mechanism, wherein the insertion mechanism is configured to place a cannula assembly in a well that is disposed on the cradle. The inserter also includes a first parts and second part, whereby the first part includes a handle and the second part comprises the entire insertion mechanism, whereby the first and second part are connected via an indentation.

20 Claims, 9 Drawing Sheets

DISPOSABLE INSERTER FOR USE WITH A MEDICAL DEVICE

CROSS REFERENCE TO RELATED APPLICATIONS

The present application is a continuation application of PCT patent application no. PCT/EP2013/001685, which has an international filing date of Jun. 8, 2013 and claims priority to U.S. Provisional Patent Application No. 61/657,771, filed on Jun. 9, 2012. The present application incorporates herein by reference the disclosure of each of the above-referenced applications in their entirety.

TECHNICAL FIELD

The present invention relates to inserters, and more particularly to systems and methods for use with a medical device.

BACKGROUND

Medical treatment of several illnesses/conditions requires drug infusion into various body compartments, for example, through subcutaneous and/or intra-venous injections. Patients suffering from Diabetes Mellitus (DM), for example, require the administration of varying amounts of therapeutic fluid, e.g., insulin, throughout the day to control their blood glucose levels. In recent years, ambulatory portable insulin infusion pumps have emerged as an alternative to multiple daily syringe injections of insulin for Type 1 diabetes patients (see, for example, Diabetes Medicine 2006; 23(2) 141-7) and subsequently for Type 2 diabetes patients (see, for example, Diabetes Metab 2007 Apr. 30 and Diabetes Obes Metab 2007 Jun. 26). Such pumps, which deliver insulin at a continuous and/or periodic basal rate as well as in bolus volumes, were developed to liberate patients from having to perform repeated self-administered injections, and to enable them to maintain a near-normal daily routine. Both basal and bolus volumes/doses have to be delivered in substantially precise doses, according to individual prescription, because an overdose or under dose of insulin could prove fatal.

SUMMARY

According to at least one embodiment of the present disclosure, a disposable inserter and method of use are disclosed. The disposable inserter in at least one embodiment is configured to be received by a skin adherable cradle for supporting an insulin pump. The exemplary disposable inserter comprises a housing comprising a cannula assembly and an insertion mechanism, two buttons concomitantly actionable for actuation of the insertion mechanism, wherein the insertion mechanism is configured to place a cannula assembly in a well disposed on the cradle; and a first part and second part, whereby the first part includes a handle and the second part comprises the entire insertion mechanism, whereby the first and second part are connected via an indentation.

In at least one embodiment of the inserter, the insertion mechanism comprises insertion and retraction springs, the springs being maintained in the housing by two latches aligned with holes disposed in the housing.

In at least one embodiment of the inserter, the inserter further comprises a protective ring which is put on the cylindrical portion of the inserter, the protective ring configured to cover the entire surface area of the two buttons. The two buttons, in at least one embodiment, are designed as torsion snap fit, whereby the torsion bar is a part of the housing. Upon actuation of the two buttons, in at least one embodiment, the buttons are tilted and the insertion spring is allowed to expand and pushes the entire mechanism assembly downwards to insert the cannula into the skin and the cannula assembly into the cradle well.

In at least one embodiment of the inserter, the springs are preloaded.

In at least one embodiment of the inserter, the inserter comprises feedback elements indicating the status of the inserter whereby a visible green protective ring indicates the inserter is unused and a visible red slider or parts of it indicate the inserter is used.

In at least one embodiment of the present disclosure, a method of inserting a cannula into a body is disclosed. The method, in at least one embodiment, comprises: placing an inserter base of an inserter on a skin adherable cradle adapted to receive a micropump, the inserter comprising a cannula assembly comprising a cannula; removing a protective ring preventing unintentional pressing of buttons on the inserter, the buttons configured to trigger an insertion mechanism; triggering the insertion mechanism by pressing concomitantly the buttons, the buttons being located on the two sides of the cylindrical portion of the inserter, the insertion mechanism inserting the cannula assembly into a well located in the cradle and further inserting the cannula of the cannula assembly into the body; and disconnecting the inserter from the cradle after insertion of the cannula In at least one embodiment of the method, the method further comprises connecting a pump to the cradle, the connecting step comprising pricking a septum of the cannula assembly with a connecting lumen provided with the micropump.

BRIEF DESCRIPTION OF THE DRAWINGS

The drawings are not intended to be limiting in any way, and it is contemplated that various embodiments of the present disclosure may be carried out in a variety of other ways, including those not necessarily depicted in the drawings. The accompanying drawings incorporated in and forming a part of the specification illustrate several aspects of embodiments of the present disclosure, and together with the description serve to explain the principles of the present disclosure; it being understood, however, that this invention is not limited to the precise arrangements shown.

DETAILED DESCRIPTION

Usage of an infusion device (e.g., insulin pump, insulin micropump) may require the adherence of a cradle to the user's skin and the insertion of a cannula into the body. The insertion of the cannula is performed by inserting a cannula assembly into a well which is located in the cradle. The cradle can be adhered to the skin via an adhesive layer which is attached to the bottom surface of the cradle. In order to insert the cannula assembly to the skin and to snap it into the well, an insertion device may be required. FIGS. 1a-1e illustrates exemplary steps (e.g., five steps) of insertion that a pump user may perform in order to prepare the infusion system for pump connection, and drug (e.g., insulin) delivery.

Figure 1A:
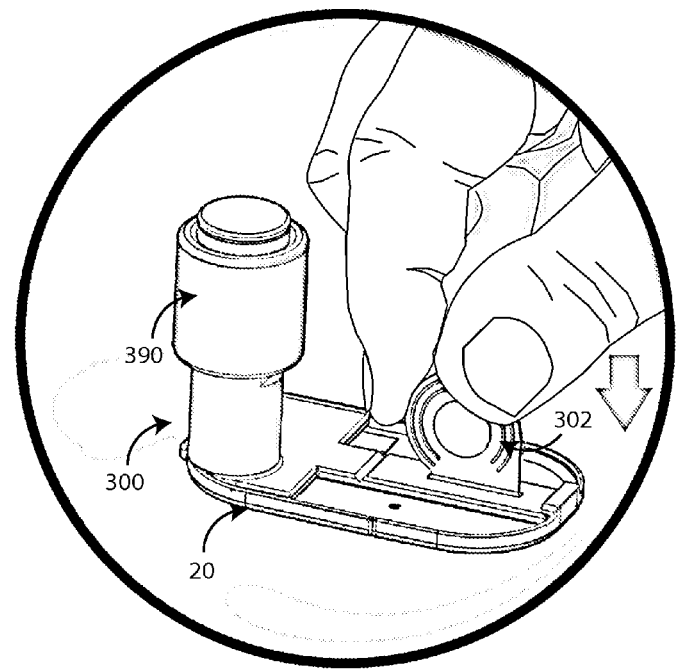
FIG. 1a illustrates the placing of the inserter and cradle on the user's skin in a chosen insertion site (e.g., lower abdomen, lower back, thigh or upper arm), according to at least one embodiment of the present disclosure.

FIG. 1a illustrates a step in which the disposable inserter 300 is placed at the user's skin, when the protective ring 390, which prevents unintentional pressing of the buttons (not shown) and undesirable insertion of the cannula, is still placed on the inserter, as safety means. The adherence of the inserter is done, while the cradle 20 is firmly fixed to the inserter 300. The user holds the entire assembly, that is, the disposable inserter and cradle by the handle 302, protruding from the cradle. The inserter is pre-loaded, therefore the user does not have to load the cannula or to insert a cannula into the inserter 300.

Figure 1B:
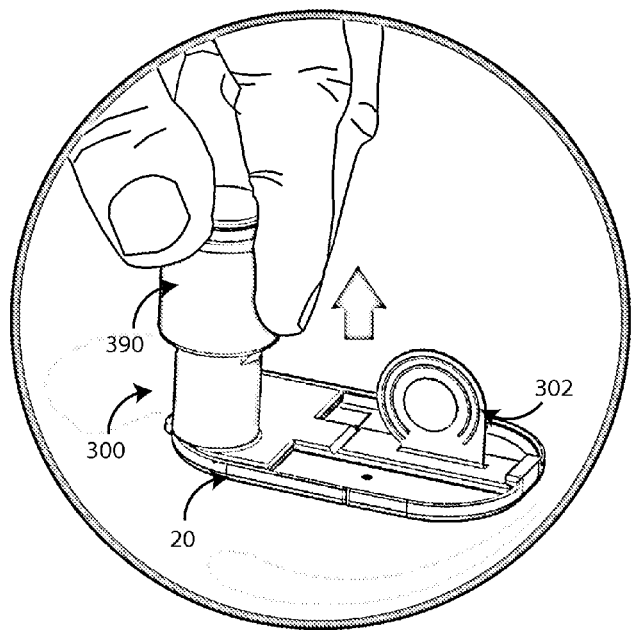
FIG. 1b illustrates the removal of a protective ring before insertion, according to at least one embodiment of the present disclosure.

FIG. 1b shows the stage of preparing the inserter for insertion stage. This stage can be performed either when the inserter is already adhered to the user skin or prior to adherence. However, placing the device with the protective ring 390 is recommended to avoid insertion due to an unintentional press. The figure shows the user pulling the protective ring 390 upwards sliding it from the cylindrical portion of the disposable inserter 300.

Figure 1C:
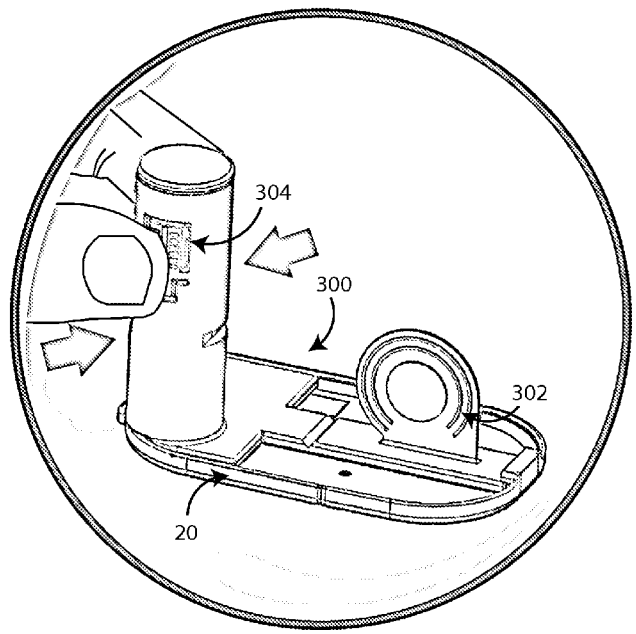
FIG. 1c illustrates the initiation of the insertion of a cannula via pressing on two buttons, according to at least one embodiment of the present disclosure.

FIG. 1c shows the user pressing both buttons 304 located on the two sides of the cylindrical portion of the inserter 300. The buttons in additional embodiments can be located at any part of the inserter 300, or cradle. Pressing both buttons, initiates the insertion of the cannula into the skin. The user must press both buttons concomitantly, in order to perform insertion. This is a safety means, to avoid unintentional insertion, in case only one button 304 is pressed. The cradle 20 and the inserter fixed to it 300, are adhered to the skin when the user presses the buttons 304.

Figure 1D:
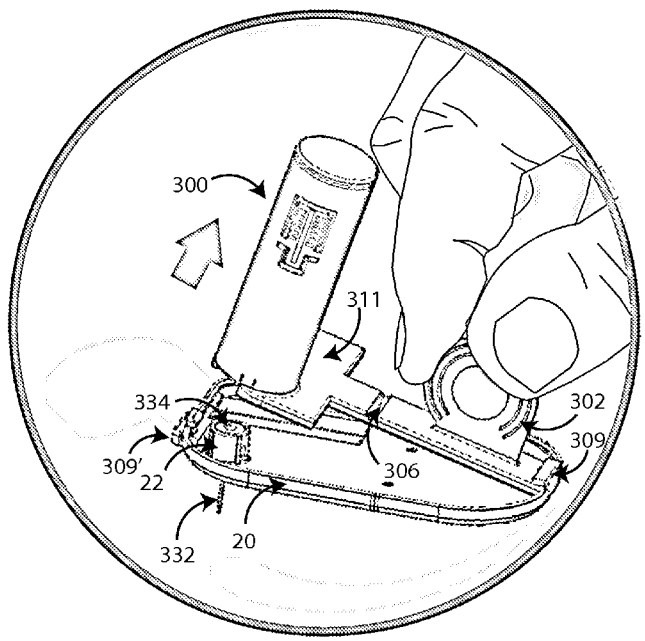
FIG. 1d illustrates the disconnection of the inserter from the cradle after cannula insertion, according to at least one embodiment of the present disclosure.

FIG. 1d shows the user releasing the disposable inserter 300, after insertion has been performed. The cannula assembly 330 was inserted into the well 22 protruding from the cradle 20. At this stage the cannula 332 made out of Teflon®, or any other bio-compatible material, is located within the skin, and the septum 334 is parallel to the upper plane of the well, allowing the connection of the micropump (not shown), and the receiving of a connecting lumen to deliver insulin from the pump into the skin via the cannula 332. The user releases the inserter from the cradle, by pulling the handle 302, upwards. A geometrical indentation 306, is designed to allow the inserter release only when the user pull the inserter up, by having a deflection upwards, folding the two parts of the inserter base 308, to release both ends of the inserter base 308 from the snaps of the cradle 309 and 309'. At this point, the entire insertion mechanism resides in the cylindrical portion of the inserter 300.

Figure 1E:
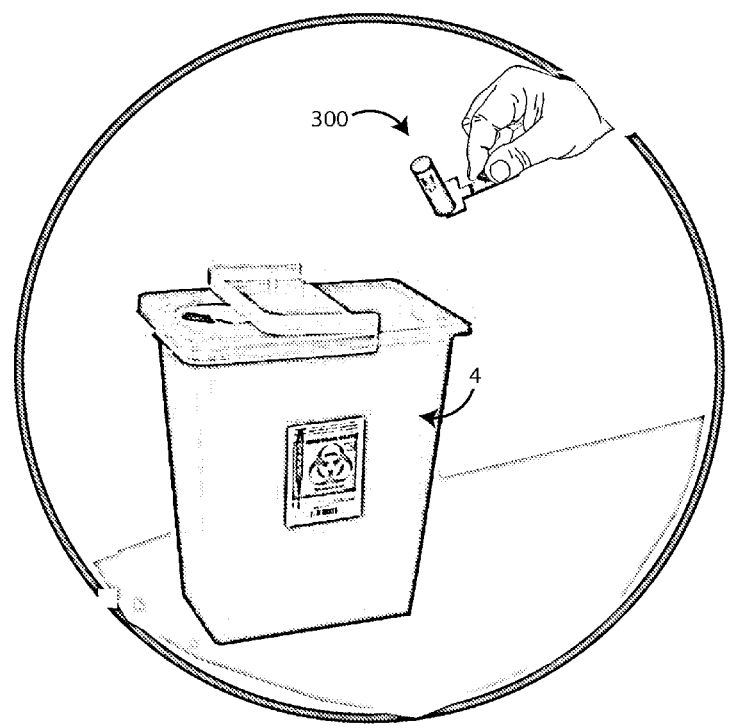
FIG. 1e illustrates disposal of the inserter after cannula insertion is completed, according to at least one embodiment of the present disclosure.

FIG. 1e shows that the user disposes the inserter, which was released in FIG. 1d into a special can for needle and inserters. The disposable inserter, when disposed has no loaded mechanisms within, there for the risk of needle pricking after insertion is reduced. Disposing the inserter, and using a new inserter, and the fact that the inserter is pre-loaded, allows the user not to deal with loading needle, and cannulas. This is a major advantage as far as risk of needle pricking.

Figure 2:
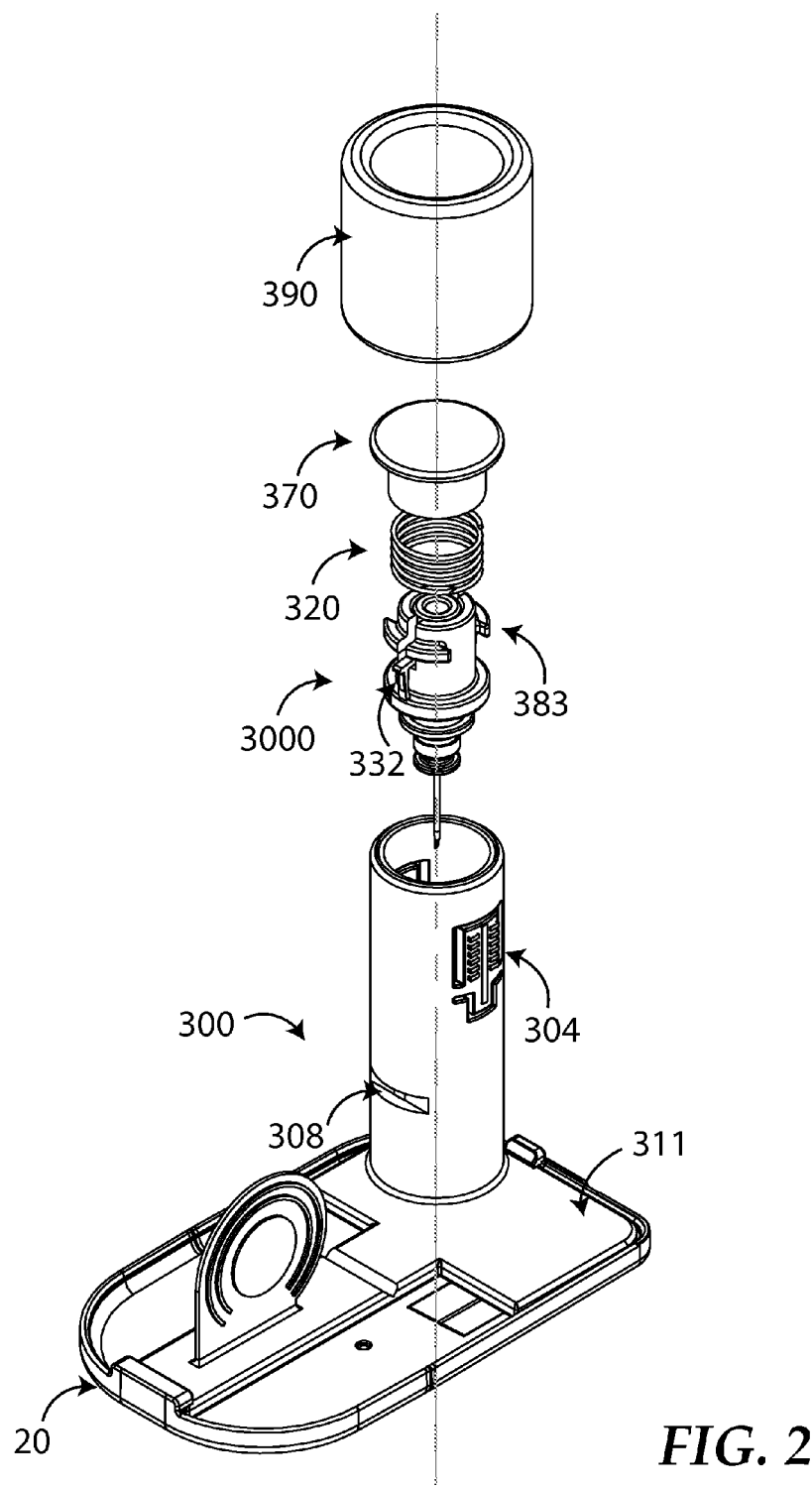
FIG. 2 illustrates an exploded view of the inserter, according to at least one embodiment of the present disclosure.

FIG. 2 shows an exploded view of the disposable insertion system, that is the disposable inserter 300 and the cradle 20. The figure shows the assembly of the different parts and subassemblies of the device. The inserter base 311 is located between the peripherals of the cradle 20. It is fixed at least 4 points of contact in order to allow a robust connection. The mechanism assembly 3000 which includes the needle assembly, retraction spring, and cannula assembly is assembled together and is put through the inner diameter of the cylindrical portion of the inserter 300. In order to allow the mechanism to function properly as will be explained further the two red slider latches 332 and 332' (not shown) are aligned with the housing holes 308 and 308'(not shown). They will allow the positioning of the red slider 330 after insertion and neutralize the insertion spring, and release the retraction spring, so that the insertion needle retraction will take place. The insertion spring 320 is placed on the upper protrusions of the red slider 338 and on the other end it is connected to the cork 370. After the inserter is closed by the cork 370, with all the components of the mechanism within, the protective ring 390 is put on the cylindrical portion of the inserter 300, so that it covers the entire surface area of the pressing buttons.

Figure 3A:
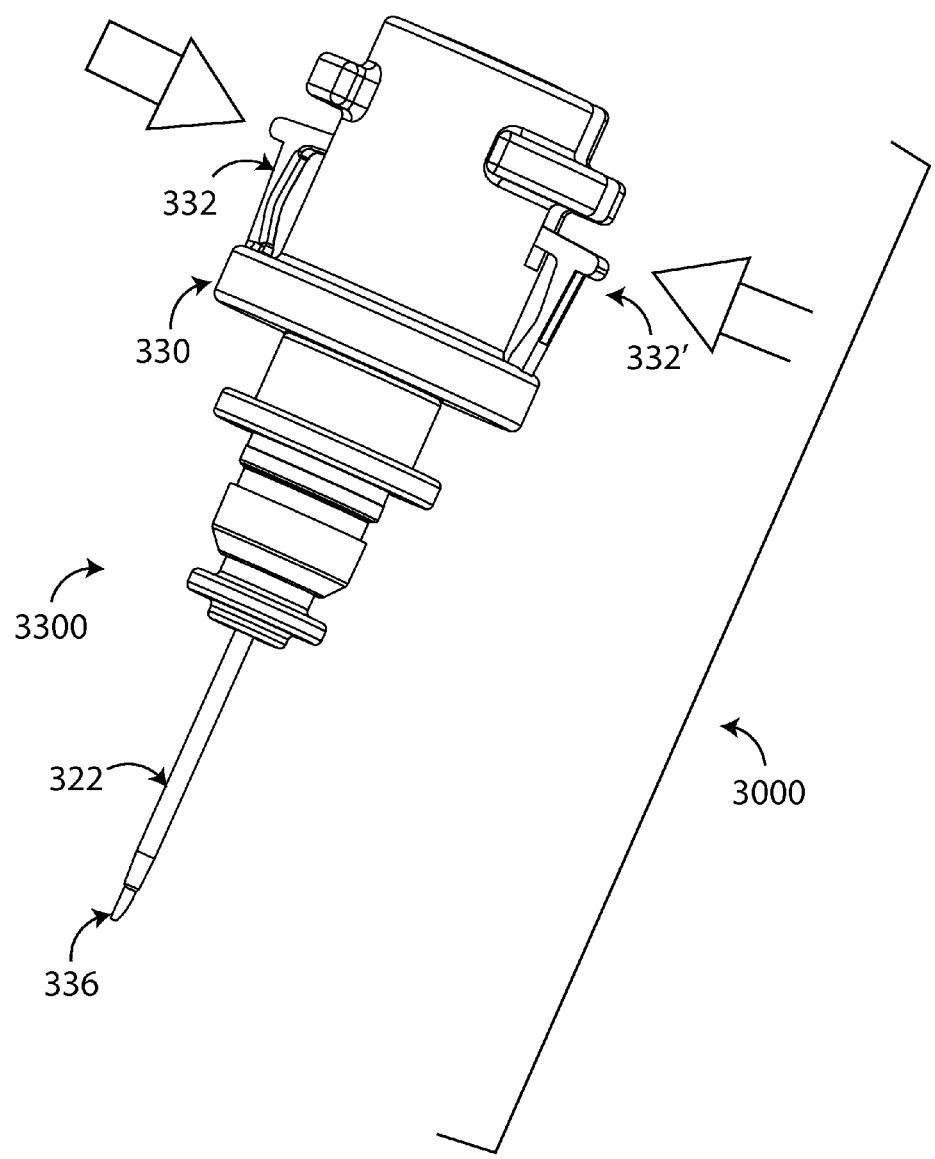
FIG. 3a illustrates a perspective view of the mechanism assembly, according to at least one embodiment of the present disclosure.

FIG. 3a shows the mechanism assembly 3000 after assembly. The needle insertion 336 goes through the cannula 322 and picks outside, so that insertion will be flawless. The entire cannula assembly 3300 is in contact with the red slider 330. The cannula cover and septum, which define the upper plane of the cannula assembly 3300 are tangent to the lower plane of the red slider 330. The cannula assembly 330 is held on the insertion needle 336 due to friction forces. During assembly, and when resides in the housing prior to insertion, the two red slider latches must be pushed inwards, as shown by the arrows in the figure, in order to hold the needle assembly (not shown) and the retraction spring (not shown) which are in a loaded position within the red slider 330.

Figure 3B:
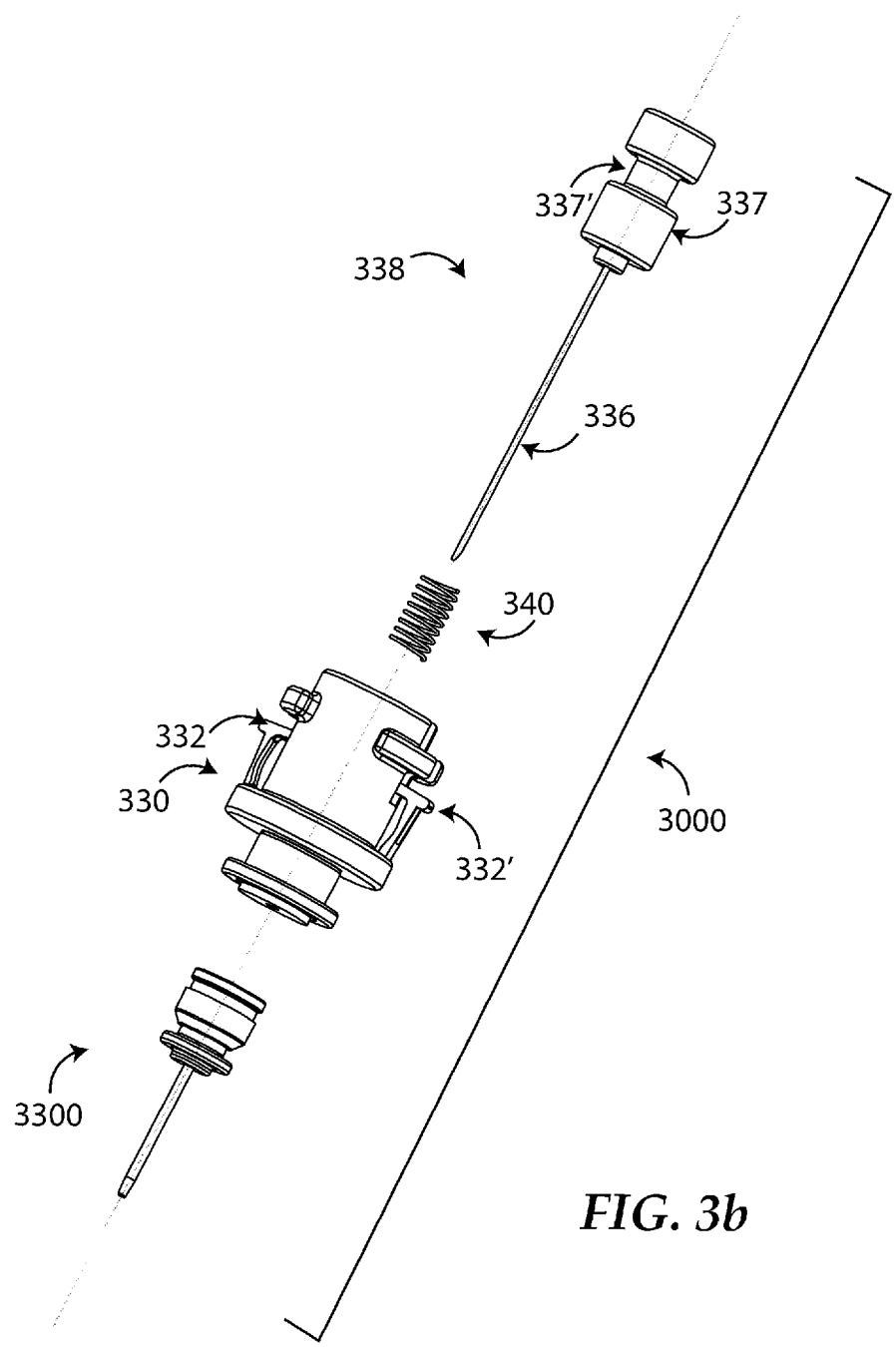
FIG. 3b illustrates an exploded view of the mechanism assembly, according to at least one embodiment of the present disclosure.

FIG. 3b shows an exploded view of the mechanism assembly 3000. The mechanism assembly includes the cannula assembly 3300, needle assembly 338 and retraction spring. The needle assembly composing the needle hub 337 and the insertion needle 336 is sliding through the red slider 330, while the retraction spring 340, is concentric to the needle assembly 338 symmetric axis. When assembled, the red slider latches must be in an opened position to allow the needle hub 337 to go through the inner diameter of the red slider until the red slider latches 332 and 332' can hold the insertion assembly 338 in the indent diameter 337' of the needle hub 337. In this position the retraction spring 340 is connected on one end to the bottom surface of the red slider 330 and to the bottom surface of the needle hub 337, and it is in a loaded position wanting to expand and retract the needle.

Figure 4A:
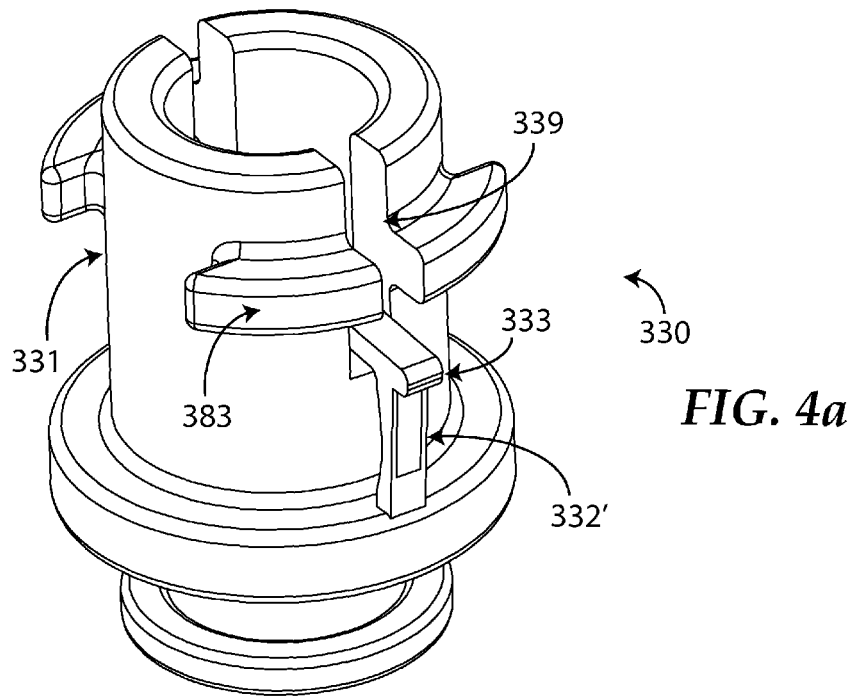
FIGS. 4a and 4b illustrate perspective views of a slider part, including its various features/elements, according to at least one embodiment of the present disclosure.

FIG. 4a shows the red slider part 330 with its features. The red slider latches 332 and 332' are the ones which are holding the needle assembly 338 and the insertion spring 340 loaded during the insertion. This is done by a force exerted inwards. The red slider latches retract and deflected outwards when they arrive to the height where the housing holes (not shown) are located. This fixes the red slider 330 in place and holding the insertion spring in a free state. And allows the retraction spring 340 to retract and pull the needle assembly 338 from the user's skin. The deflection of the red slider latches 332 and 332' is allowed due to the through hole 339 of the red slider 330. The bulges 333 and 333' are aiding the grip of the red slider latches in the housing holes when insertion ended and cannula assembly is in the well. The protrusions of the red slider 383, are supports for the insertion spring 320. The indent 331 is to allow the press buttons 304 to be deflected with no interference.

Figure 4B:
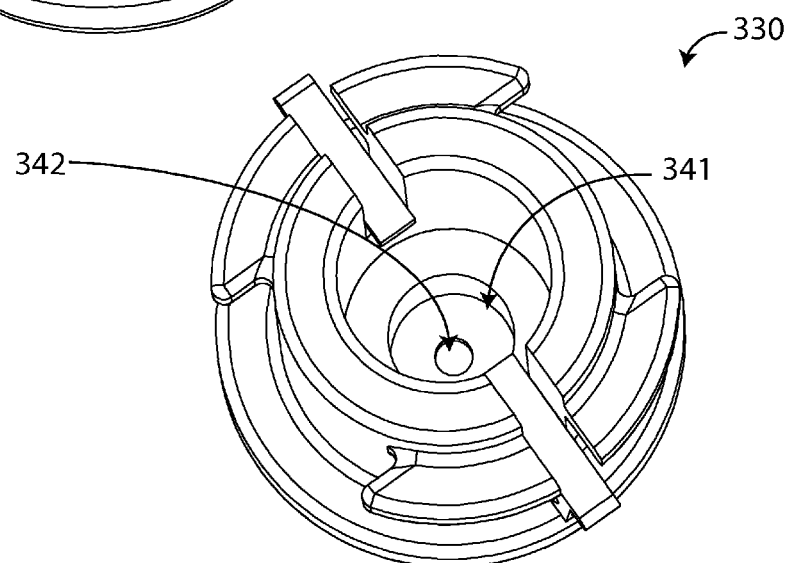

FIG. 4b shows the inner volume of the red slider 330. The insertion needle 336 can go through the red slider through a hole 342 and then the cannula assembly 3300 can be connected. Indent 341 is a dedicated support for the retraction needle 340 in the red slider 330 while in a loaded state.

Figures 5A, 5B:
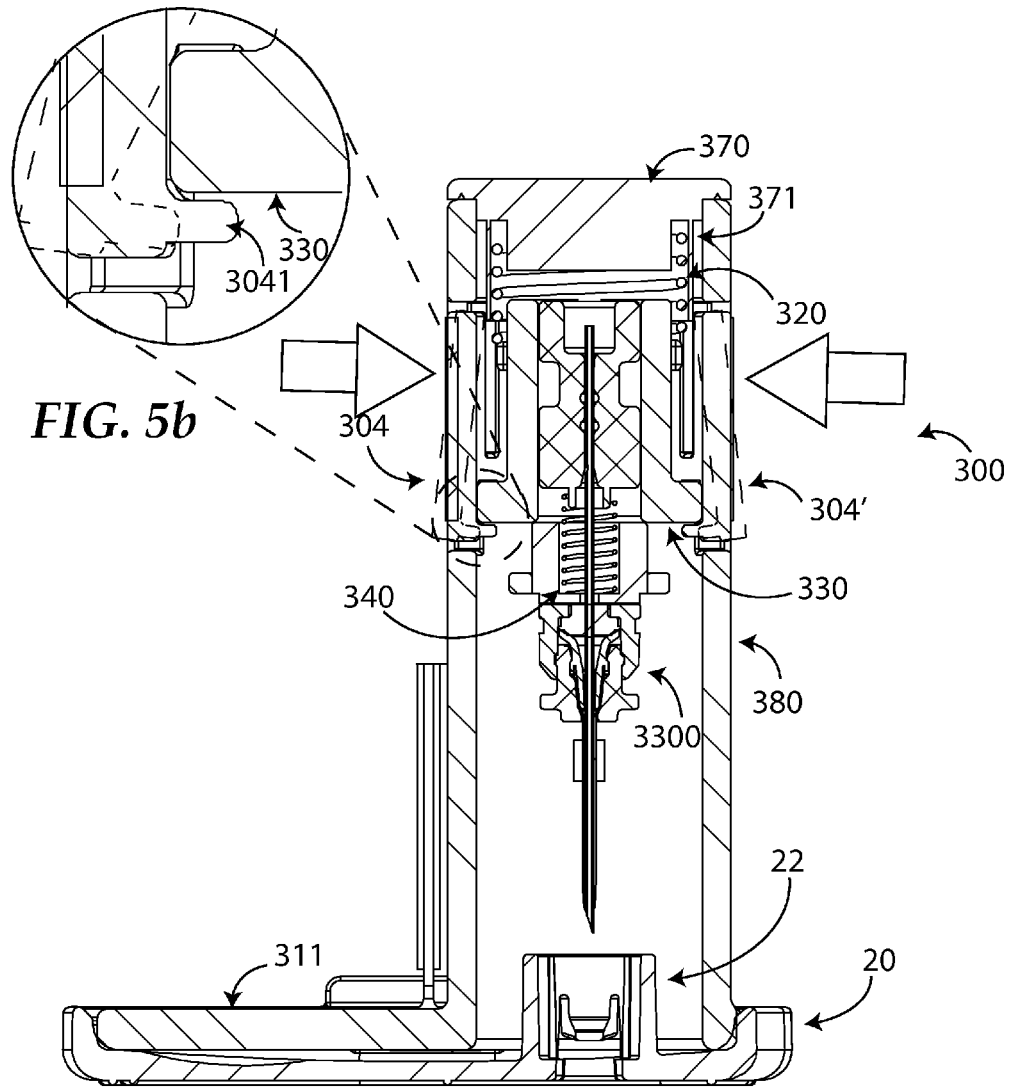
FIG. 5a illustrate a cross section view of the inserter in a loaded position (e.g., upon initiation of insertion), according to at least one embodiment of the present disclosure.
FIG. 5b illustrates an enlarged view of the pressing of the buttons and showing the support and release of the slider, according to at least one embodiment of the present disclosure.

FIG. 5a shows a cross section view of the inserter 300 in a loaded position. This state is prior to insertion initiation. The user presses both buttons 304 and 304' in order to insert the cannula into the skin. Exerting force on the buttons, will tilt the buttons. The buttons 304 and 304' are designed as torsion snap fit, which its torsion bar is a part of the housing 380. Before the user press the buttons, the mechanism assembly and the red slider 300 in particular rests on the two protrusion snaps 3041 as shown in FIG. 5b. When the user exert force, the buttons tilt and allow the insertion spring 320 to expand and to push the entire mechanism assembly downwards to insert the cannula into the skin and the snap the cannula assembly 3300 into the cradle well 22. In order to prevent interference of the buttons with the mechanism, more specifically, to contact the insertion spring 320, a protective wall 371 was design in the cork 370 to limit the motion and deflection of the buttons 304 and 304'.

Figure 5C:
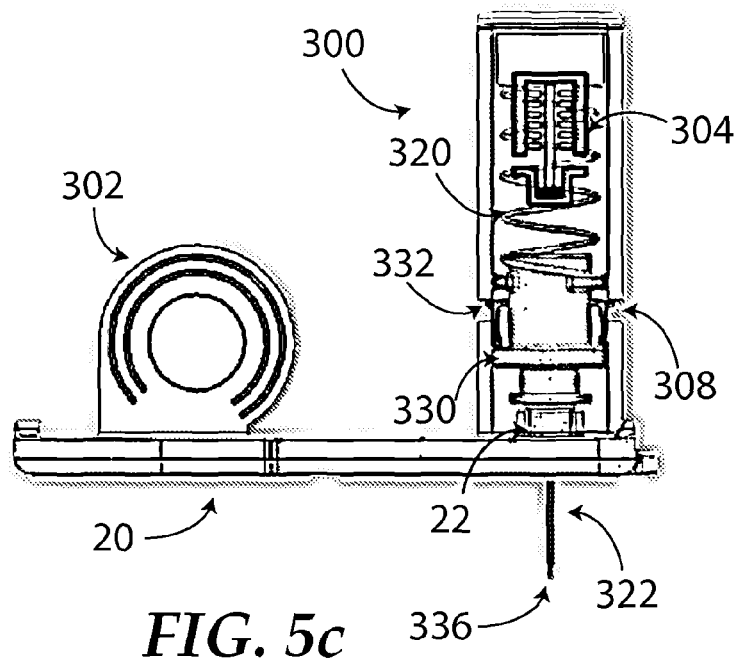
FIG. 5c illustrates the inserter when the cannula is inserted and the slider latches are fixed/engaged in the housing holes/grooves, according to at least one embodiment of the present disclosure.
Figure 5D:
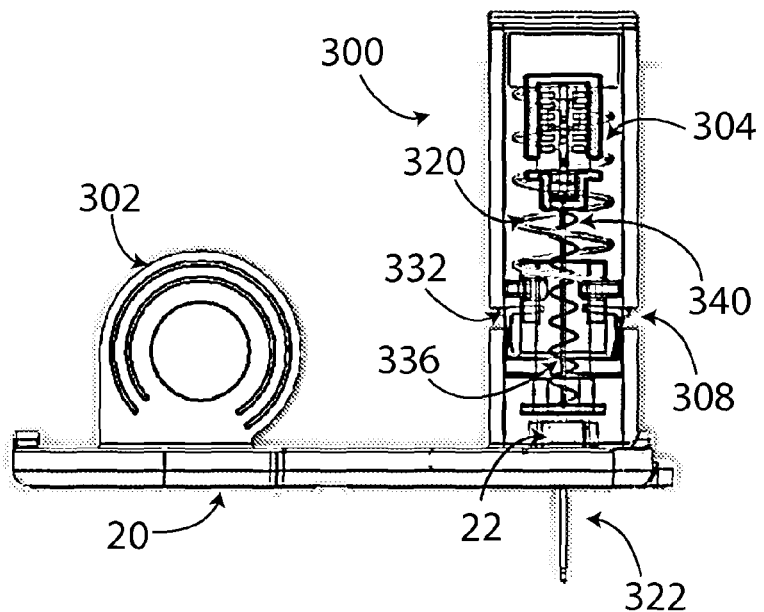
FIG. 5d illustrates the retraction of the needle assembly, while the slider is fixed/in place, according to at least one embodiment of the present disclosure.

FIG. 5c shows the inserter 300, in the insertion phase. The cannula assembly 3300 is inserted into the cradle well 20. The buttons 304 and 304' were pressed and the red slider 330 moved downwards due to the insertion spring 430 which pushed the mechanism assembly down. The red slider latches 332 and 332' are fixed in the housing holes 308 and 308' using the bulges 333 and 333' we described in FIG. 4a. In this state, both the cannula 322 and the insertion needle 336 are inserted to the skin. The design determines that in this state the insertion spring is in its free state and it is neutralized both by the red slider latches 332 and 332' fixed in the housing holes 308 and 308, and due to the design of spring selection.

FIG. 5c shows the retraction phase. The cannula 322 is inserted and the cannula assembly 3300 is fixed in the cradle well 22. However the needle assembly 338 is retracted automatically. The fixation of the two red slider latches 332 and 332' in the housing holes 308 and 308' due to their aspiration to return to their initial state and shape in which they were manufactured, releases the grip the two red slider latches 332 and 332' held to the needle hub 337. Therefore, the retraction spring 340 expands and pushes the needle assembly 338 upwards, retracting the needle from the user's skin and cannula volume 22. The design will take a safety factor to the retraction displacement to make sure that a full retraction was operated. In this state both the retraction spring 340 and insertion spring 320 are in a free state. After this operating step of retraction, the user can disconnect the inserter 300 from the cradle 20 and continue according to FIG. 1d-1e, as depicted.

There is disclosed a disposable inserter adapted to be received by a skin adherable cradle for supporting an insulin pump, the disposable inserter comprising: a housing comprising a cannula assembly and an insertion mechanism; two buttons concomitantly actionable for actuation of the insertion mechanism, wherein the insertion mechanism is adapted to place a cannula assembly in a well disposed on the cradle.

In at least one embodiment, the insertion mechanism comprises insertion and retraction springs, the springs being maintained in the housing by two latches aligned with holes disposed in the housing.

In at least one embodiment, the disposable inserter further comprises a protective ring 390 which is put on the cylindrical portion of the inserter 300, so that to cover the entire surface area of the two buttons.

In at least one embodiment, the buttons are designed as torsion snap fit, whereby the torsion bar is a part of the housing.

In at least one embodiment, upon actuation of the buttons the buttons are tilted and the insertion spring 320 is allowed to expand and to push the entire mechanism assembly downwards to insert the cannula into the skin and the cannula assembly 3300 into the cradle well 22.

In at least one embodiment, the springs are preloaded.

In at least one embodiment, the disposable inserter comprises two parts whereby the first part includes a handle and the second part comprising the entire insertion mechanism whereby the first and the second part are connected via an indentation In at least one embodiment, the disposable inserter comprises feedback elements indicating the status of the inserter whereby a visible green protective ring indicates the inserter is unused and a visible red slider or parts of it indicate the inserter is used.

There is disclosed a method of inserting a cannula into a body, comprising the steps of: placing an inserter base 308 of an inserter 300 on a skin adherable cradle adapted to receive a micropump, the inserter comprising a cannula assembly comprising a cannula; removing a protective ring 390 preventing unintentional pressing of buttons triggering a insertion mechanism; triggering the insertion mechanism by pressing concomitantly two buttons 304 and 304', the buttons being preferably located on the two sides of the cylindrical portion of the inserter 300, the insertion mechanism inserting the cannula assembly into a well located in the cradle and further inserting the cannula of the cannula assembly into the body; disconnecting the inserter 300 from the cradle 20 after insertion of the cannula (by pulling upwards a handle 302).

In at least one embodiment, the method further comprises the step of connecting a pump to the cradle, the connection pricking a septum 334 of the cannula assembly with a connecting lumen 102 provided with the micropump.

There is disclosed an inserter comprising two parts whereby the first part includes a handle and the second part comprising the entire insertion mechanism whereby the first and the second part are connected via an indentation There is disclosed an inserter comprising feedback elements indicating the status of the inserter whereby a visible green protective ring indicates the inserter is unused and a visible red slider or parts of it indicate the inserter is used.
336 Insertion needle 337 Needle hub
338 Needle assembly
330 Red slider
311 inserter base
3000 Mechanism assembly
370 Cork
332 and 332' Red slider latches
308 and 308' Housing holes
383 Protrusions of red slider
304 Pressing buttons
322 Cannula
3300 Cannula assembly
337' Indent diameter of needle hub
340 Retraction spring

The invention claimed is:

1. A disposable inserter configured to be received by a skin adherable cradle for supporting an insulin pump, the disposable inserter comprising:
a housing comprising a cannula assembly and an insertion mechanism;
two buttons concomitantly actionable for actuation of the insertion mechanism, wherein the insertion mechanism is configured to place a cannula assembly in a well disposed on the skin adherable cradle; and
an inserter base having a first part and second part, whereby the first part includes a handle and the second part comprises the insertion mechanism, whereby the first and second part are connected via an indentation, and the first part and second part fold about the indentation when the handle is pulled to release the inserter base from the skin adherable cradle.

2. The disposable inserter of claim 1, wherein the insertion mechanism comprises insertion and retraction springs, the springs being maintained in the housing by two latches aligned with holes disposed in the housing.

3. The disposable inserter of claim 1, further comprising a protective ring which is put on a cylindrical portion of the insertion mechanism, the protective ring configured to cover the entire surface area of the two buttons.

4. The disposable inserter of claim 1, wherein the two buttons are designed as torsion snap fit, whereby a torsion bar is a part of the housing.

5. The disposable inserter of claim 2, wherein upon actuation of the two buttons the buttons are tilted and the insertion spring is allowed to expand and to push the insertion mechanism downwards to insert the cannula into the skin and the cannula assembly into the cradle well.

6. The disposable inserter of claim 2, wherein the springs are preloaded.

7. The disposable inserter of claim 1, comprising feedback elements indicating the status of the insertion mechanism whereby a visible green protective ring indicates the insertion mechanism is unused and a visible red slider or parts of it indicate the insertion mechanism is used.

8. A method of inserting a cannula into a body, comprising:
placing an inserter base of an inserter on a skin adherable cradle adapted to receive a micropump, the inserter comprising a cannula assembly having a cannula and the inserter base having a first part and second part, whereby the first part includes a handle and the second part comprises an insertion mechanism, whereby the first and second part are connected via an indentation;
removing a protective ring preventing unintentional pressing of buttons on the inserter, the buttons configured to trigger the insertion mechanism;
triggering the insertion mechanism by pressing concomitantly the buttons, the buttons being located on the two sides of a cylindrical portion of the inserter, the insertion mechanism inserting the cannula assembly into a well located in the cradle and further inserting the cannula of the cannula assembly into the body; and
disconnecting the inserter from the cradle after insertion of the cannula via pulling the handle and causing the first part and second part to fold about the indentation which releases the inserter base from the skin adherable cradle.

9. The method of claim 8, further comprising connecting the micropump to the cradle, the connecting step comprising pricking a septum of the cannula assembly with a connecting lumen provided with the micropump.

10. The method of claim 8, wherein inserting the cannula assembly into the well located in the cradle places a septum of the cannula assembly parallel to an upper plane of the well.

11. The method of claim 8, wherein placing the inserter base of the inserter on the skin adherable cradle further comprises engaging ends of the inserter base in snaps of the cradle.

12. The method of claim 8, wherein disconnecting the inserter from the cradle is via pulling the handle away from the cradle to both deflect upwards and fold the first and second parts of the inserter base, thereby releasing ends of the inserter base from snaps of the cradle.

13. The method of claim 8, further comprising indicating the status of the insertion mechanism via feedback elements of the inserter.

14. The method of claim 8, wherein triggering of the two buttons tilts the buttons which causes an insertion spring to expand and push the insertion mechanism downwards to insert the cannula into the body and the cannula assembly into the cradle well.

15. The method of claim 8, further comprising automatically retracting a needle assembly of the insertion mechanism into the cylindrical portion of the inserter after inserting the cannula assembly into a well located in the cradle and further inserting the cannula of the cannula assembly into the body.

16. The disposable inserter of claim 1, wherein the handle protrudes from the first part.

17. The disposable inserter of claim 1, wherein ends of inserter base are configured to engage snaps of the cradle.

18. The disposable inserter of claim 1, wherein the inserter base has four points of contact by which to engage the skin adherable cradle.

19. The disposable inserter of claim 1, wherein the indentation is geometrically designed to allow the inserter to release from the cradle only when the handle is pulled away from the cradle to both deflect upwards and fold the first and second parts of the inserter base.

20. The disposable inserter of claim 1, wherein the indentation is geometrically designed to allow the inserter to release from the cradle only when the handle is pulled away from the cradle to both deflect upwards and fold the first and second parts of the inserter base which releases both ends of the inserter base from snaps of the cradle.

* * * * *